United States Patent [19]

Dovichi et al.

[11] Patent Number: 5,567,294
[45] Date of Patent: Oct. 22, 1996

[54] MULTIPLE CAPILLARY BIOCHEMICAL ANALYZER WITH BARRIER MEMBER

[75] Inventors: Norman J. Dovichi; Jian Z. Zhang, both of Edmonton, Canada

[73] Assignee: Board of Governors, University of Alberta, Alberta, Canada

[21] Appl. No.: 593,877

[22] Filed: Jan. 30, 1996

[51] Int. Cl.$^6$ .......................... G01N 27/26; G01N 27/447
[52] U.S. Cl. ............................ 204/603; 204/452
[58] Field of Search .................. 204/603, 452, 204/600, 602, 604, 605, 451, 453, 454, 455; 73/61.58

[56] References Cited

U.S. PATENT DOCUMENTS

| | | | |
|---|---|---|---|
| 5,274,240 | 12/1993 | Matties et al. | 204/603 X |
| 5,324,401 | 6/1994 | Yeung et al. | 204/603 X |
| 5,366,608 | 11/1994 | Kambara | 204/603 |
| 5,439,578 | 8/1995 | Dovichi et al. | 204/603 |
| 5,468,364 | 11/1995 | Fuji | 204/603 |

*Primary Examiner*—Kathryn Gorgos
*Assistant Examiner*—John S. Starsiak, Jr.
*Attorney, Agent, or Firm*—McDermott, Will & Emery

[57] ABSTRACT

A multiple capillary biochemical analyzer for sequencing DNA and performing other analyses, in which a set of capillaries extends from wells in a microtiter plate into a cuvette. In the cuvette the capillaries are held on fixed closely spaced centers by passing through a sandwich construction having a pair of metal shims which squeeze between them a rubber gasket, forming a leak proof seal for an interior chamber in which the capillary ends are positioned. Sheath fluid enters the chamber and entrains filament sample streams from the capillaries. The filament sample streams, and sheath fluid, flow through aligned holes in a barrier member spaced close to the capillary ends, into a collection chamber having a lower glass window. The filament streams are illuminated above the barrier member by a laser, causing them to fluoresce. The fluorescence is viewed end-on by a CCD camera chip located below the glass window. The arrangement ensures an equal optical path length from all fluorescing spots to the CCD chip and also blocks scattered fluorescence illumination, providing more uniform results and an improved signal to noise ratio.

13 Claims, 3 Drawing Sheets

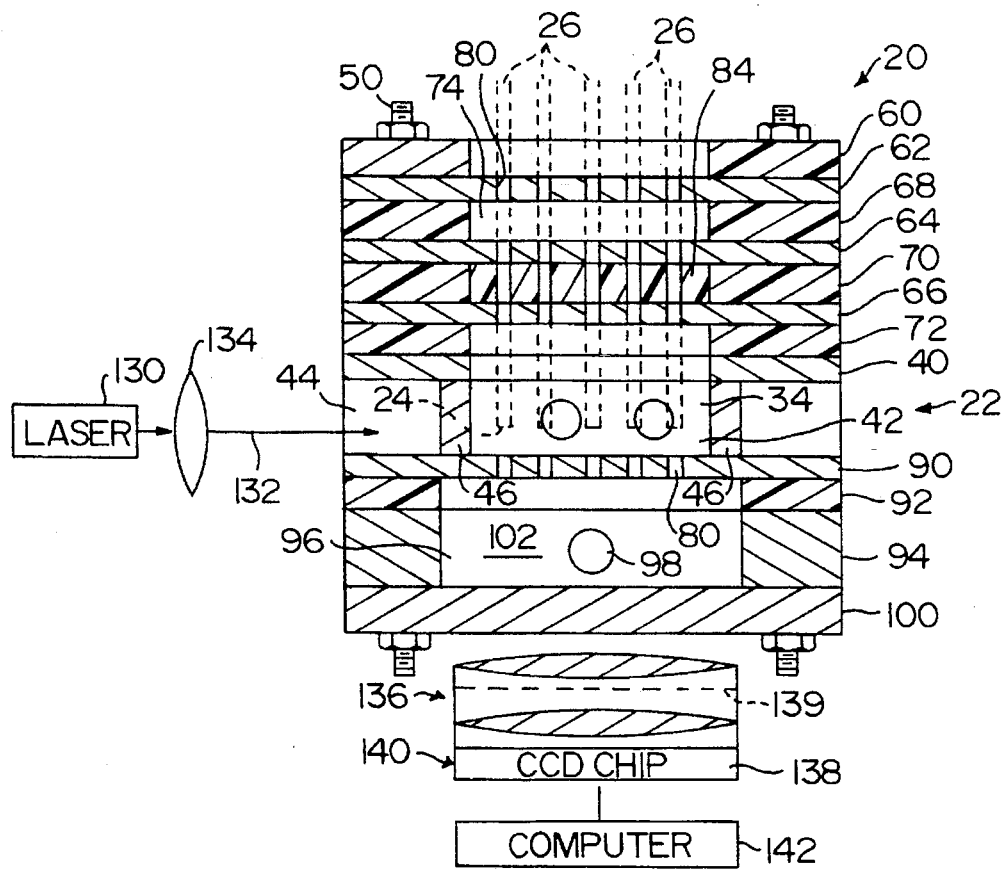
FIG. 2
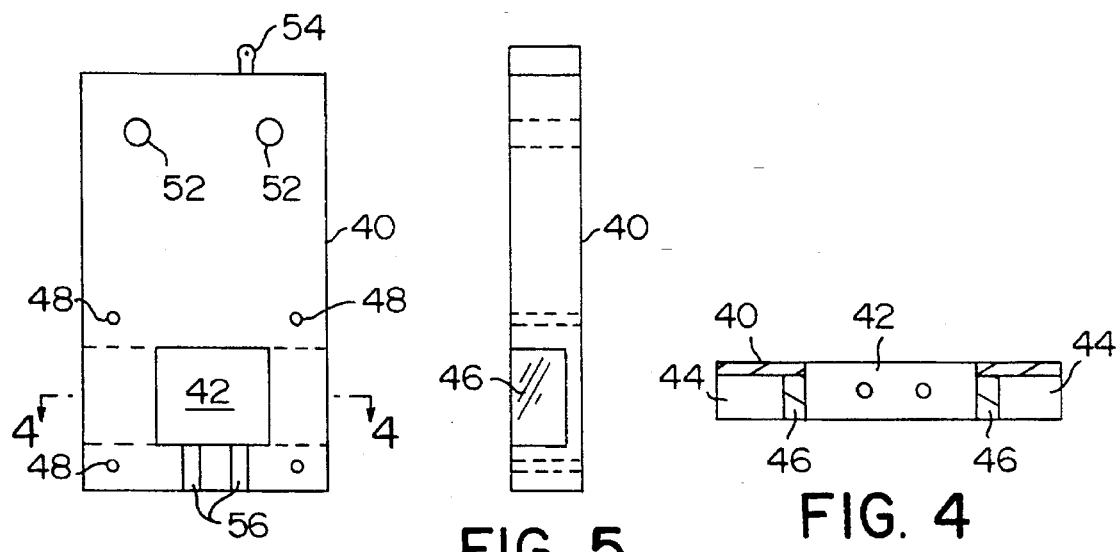
FIG. 3
FIG. 5
FIG. 4

MULTIPLE CAPILLARY BIOCHEMICAL ANALYZER WITH BARRIER MEMBER

FEDERAL RIGHTS IN THE INVENTION

The U.S. government has rights in this invention pursuant to grant number DE-FG02-92ER61123 awarded by the U.S. Department of Energy.

FIELD OF THE INVENTION

This invention relates to method and apparatus used for biochemical analysis.

BACKGROUND OF THE INVENTION

Simultaneous analysis of a large number of biological samples is useful in various types of analysis, for example, flow cytometry, DNA sequencing, liquid chromatography, oligonucleotide analysis, and various electrophoretic techniques. Rapid DNA analysis is of particular importance in the Human Genome Project, which is an attempt to identify the sequence of bases in human DNA.

One technique that has been applied to the sequencing of DNA is capillary electrophoresis. In this technique, an appropriate solution is polymerized or gelled to form a porous matrix in a fused silica capillary tube of internal dimensions in the order of 50 μm. An electric field is then applied across the matrix. Fragments of sampled DNA injected into one end of the capillary tube migrate through the matrix under the effect of the electric field at speeds that depend on the length of the fragment. Therefore, different length fragments arrive at a detection part of the capillary at different times. The dideoxynucleotide at one end of the fragment may be labelled with a fluorescent marker during a reaction step. The fluorescent marker is associated with the terminating dideoxynucleotide. When the fragment passes through a beam of light from a laser in a detection zone, the fluorescent marker fluoresces and the fluorescence may be detected as an electric signal. The intensity of the electric signal depends on the amount of fluorescent marker present in the matrix in the detection zone. The dideoxynucleotide at the end of the fragment may then be identified by a variety of methods. As different length fragments migrate through the matrix under the applied field, a profile of the fragments may be obtained.

A multiple capillary biochemical analyzer for use in capillary electrophoresis and for other applications is disclosed in our U.S. Pat. No. 5,439,578 issued Aug. 8, 1995. In that patent a multiple capillary analyzer is disclosed which, among its other features, discloses detection of light from multiple capillaries which terminate in a flow chamber. Sheath fluid entrains individual sample streams from the capillaries, and collimated sample excitation radiation is applied simultaneously across the ends of the capillaries. Light emitted from the excited sample is detected by an optical detection system. The disclosure and drawings of said patent are hereby incorporated in their entirety by reference into this specification.

In one embodiment of the analyzer disclosed in the above-identified patent, the rows of capillaries are offset, with the furthest back row of capillaries furthest downstream, so that the rows of capillaries in effect form a staircase. This offset configuration allows samples migrating from a number of rows of multiple capillaries to be imaged simultaneously, without overlap, onto photo detectors. Imaging occurs through one of the walls of the cuvette.

There are several disadvantages to the staircase configuration disclosed. First, the rows of capillaries in the back of the cuvette are imaged through a millimeter or more of sheath fluid, while the capillaries in the front of the cuvette are imaged through only a few micrometers of fluid. The resultant difference in optical path lengths leads to optical aberration. While the aberration can be largely corrected by including a prism in the optical train, it cannot easily be entirely corrected.

Secondly, stray laser light illuminates the capillaries, leading to background light scatter and fluorescence. While careful adjustment of the illumination conditions can be used to try to correct this problem, a two-dimensional array of capillaries is inherently more sensitive to light scatter than a single dimensional array of capillaries. However a two-dimensional array is preferred so that samples from a larger number of capillaries can simultaneously be analyzed.

Thirdly, it is desirable for the capillaries to be uniformly spaced, to obtain good sheath flow and uniformly spaced sample streams, and so that the position of each fluorescence spot will be known and will not overlap a non-fluorescing spot. Achievement of this uniform spacing is extremely difficult to obtain.

Accordingly, it is an object of the invention in one of its aspects to produce a multiple capillary analyzer which can alleviate some of the above disadvantages. To this end the invention provides in one of its aspects an analyzer for analyzing an organic sample, said analyzer comprising:

(a) a plurality of capillary tubes arranged side by side, each capillary tube having first and second ends, the second ends of the capillary tubes terminating adjacent each other and the first ends being connectable to a source of organic sample, (b) a flow chamber having an interior cavity, the second ends of the capillary tubes terminating inside the interior cavity, (c) means to force said organic sample through the capillary tubes from the first ends of the capillary tubes to the second ends of the capillary tubes, (d) means to provide sheath fluid into the interior cavity of said flow chamber to provide a flow of sheath fluid past the second ends of the capillary tubes and for entraining organic sample from said capillary tubes in individual sample streams from the second ends of the capillary tubes, (e) a barrier member spaced from the second ends of said capillary tubes, said barrier member including a plurality of openings therein, said openings being aligned with said second ends of said capillary tubes for the individual sample streams therefrom to pass through said openings, said barrier member having a first side facing said second ends of said capillary tubes, and a second side opposite said first side, (f) radiation means providing electromagnetic radiation having a wavelength that may excite said sample to emit radiation, said radiation means being positioned to illuminate said sample streams between said second ends of said capillary tubes and said first side of said barrier member, (g) and radiation detection means on said second side of said barrier means for detecting radiation which is emitted from said sample streams and which passes through said openings to said second side of said barrier member.

Further objects and advantages of the invention will appear from the following description, taken together with the accompanying drawings.

BRIEF DESCRIPTION OF THE DRAWINGS

In the drawings:

FIG. 2 is a cross-sectional view of a portion of the analyzer of FIG. 1;

FIG. 3 is a plan view of a plate of the analyzer portion of FIG. 2;

FIG. 4 is a cross-sectional view along lines 4—4 of FIG. 3;

FIG. 5 is an edge view of the plate of FIGS. 3 and 4;

DETAILED DESCRIPTION OF PREFERRED EMBODIMENTS

Figure 1:
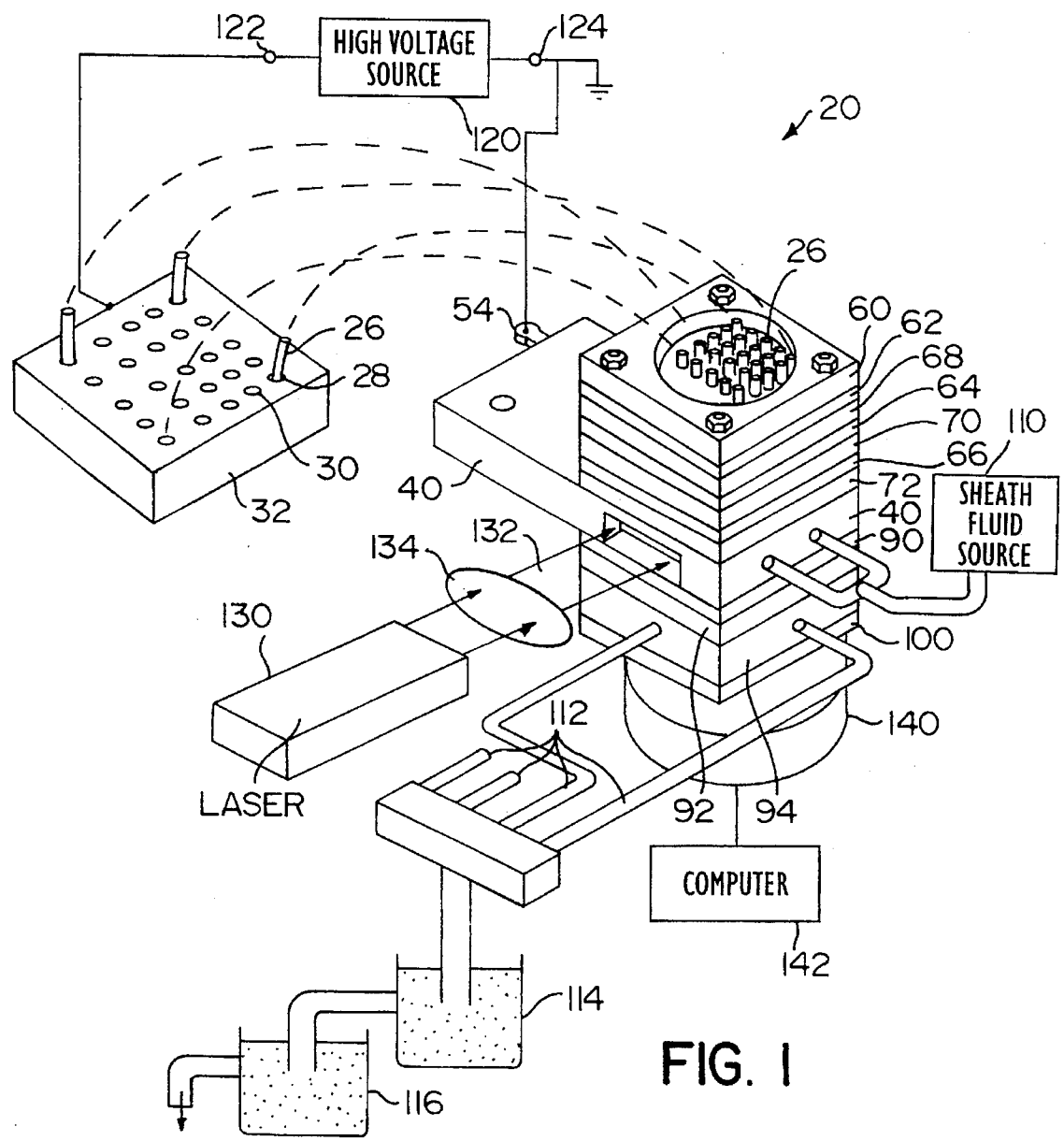
FIG. 1 is a diagrammatic view of an analyzer system according to the invention.

Reference is first made to FIGS. 1 and 2, which show an analyzer 20 for analyzing an organic sample such as DNA. The analyzer 20 includes a sheath flow cuvette 22 enclosing the ends 24 (shown in dotted lines in FIG. 2) of a set of capillary tubes 26.

The capillary tubes 26 are arranged in a generally rectangular array, which in the example shown is an array of five tubes by five tubes. The other ends 28 of the capillary tubes 26 terminate in twenty-five wells 30 of a conventional microtiter plate 32.

The capillary tubes 26 are conventional fused silica capillaries, having an inner diameter of about 50 μm and an outer diameter of about 150 μm, and are available from many conventional commercial sources. The fluid in the wells 30 contains the samples to be analyzed (a different sample in each well).

The ends 24 of the capillaries 26 which are located in the cuvette 22 are positioned in an interior chamber 34 (FIG. 2) in the cuvette 22. The capillary ends 24 are held in position in the chamber 34 in a leak-proof manner by a sandwich construction for the cuvette 22. The sandwich construction will now be described.

The cuvette 22 includes a rectangular stainless steel plate 40, which in one example was 29 mm by 59 mm and 5 mm thick, with a 13 mm by 13 mm opening 42. The opening 42 defines the bulk of the chamber 34. Plate 40 is also shown in FIGS. 3 to 5. Two grooves 44 are milled in one side of the plate 40, each about 4 mm thick, extending from the opening 42 to the edges of the plate. Two glass windows 46 each 12 mm by 4 mm are glued into the groove bordering each side of the opening 42. The windows 46 are for a laser beam to enter and leave chamber 34, as will be described.

Plate 40 also includes four bolt holes 48 arranged in a square configuration, through which bolts 50 (FIG. 2) may pass, to hold the sandwich construction together. Plate 50 also includes two openings 52 to allow the cuvette to be mounted on a mounting fixture (not shown) and a tab 54 for connection of a ground wire (as will be described). Plate 40 also includes two tubular openings 56 (e.g. 3.3 mm diameter) for sheath fluid to enter chamber 34.

Figure 6:
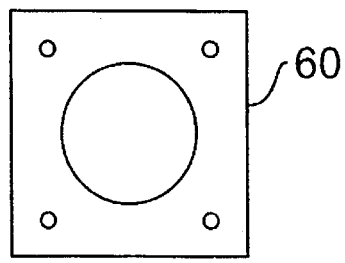
FIG. 6 is a plan view of a top cap of the analyzer portion of FIG. 2.
Figure 8:
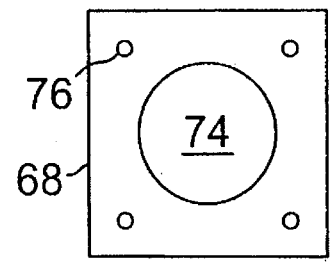
FIG. 8 is a plan view of a washer of the analyzer portion of FIG. 2.
Figure 7:
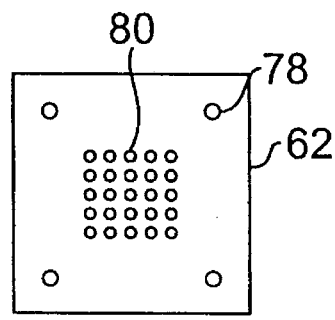
FIG. 7 is a plan view of a shim of the analyzer portion of FIG. 2.

Mounted above the plate 40 is a stack comprising a stainless steel cap 60 (also shown in FIG. 6), and three identical stainless steel shims 62, 64, 66 (FIG. 7), each separated by identical plastic (e.g. TEFLON™) washers 68, 70 (FIG. 8). A third identical plastic (e.g. TEFLON™) washer 72 separates shim 66 from metal plate 40. The washers 68, 70, 72 help to prevent leaks. Each washer in the example described is 29 mm by 29 mm and 1 mm to 2 mm thick, each with a central circular opening 74, and four bolt holes 76 for bolts 50.

Each stainless steel shim 62, 64, 66 includes four bolt holes 78 and a five by five array of holes 80 for the capillary tubes 26. The holes 80 may be formed by any known technique, e.g. drilling, ultrasonic molding, or electroforming, and are each of the same diameter as the outer capillary diameter (e.g. 150 μmeter). The holes 80 are preferably normally spaced as closely together as possible, consistent with having sufficient material between them to provide sufficient mechanical strength to hold the capillary tubes. Preferably the spacing between holes 80 does not exceed about one outer diameter of the capillary tubes. If the spacing is too large, it may be difficult to focus the laser beam (to be described) over the large area defined by widely spaced capillaries, and collection of light from a large area may also be more difficult.

Figure 9:
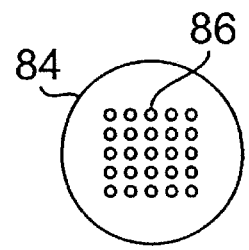
FIG. 9 is a plan view of a rubber gasket of the analyzer portion of FIG. 2.

Located in the central opening 74 of the washer 70 is a circular silicon rubber disc or gasket 84 (FIG. 9), which is of slightly greater thickness than that of washer 70. The disc 84 also contains a five by five array of holes 86 for the capillary tubes 26. Each hole 86 may be formed by piercing the disc 84 with a capillary when the disc is assembled in the stack, thus ensuring that holes 86 will be of the same diameter as the outer capillary diameter. When the stack is assembled, the rubber disc 84 is compressed between the adjacent metal shims 64, 66, thus providing a leak proof seal around the capillary tubes 26 at the top of the chamber 34.

Looking below the plate 40, a further thin metal shim or barrier member 90 is glued to the bottom of plate 40 (and to the windows 46). Shim or barrier member 90 is exactly the same as shims 62, 64, 66 and has the same bolt holes 78 and the same holes 80, which are precisely aligned with holes 80 in shims 62, 64, 66.

Figure 10:
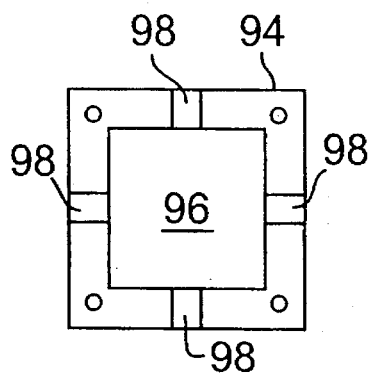
FIG. 10 is a plan view of a bottom plate of the analyzer portion of FIG. 2.

Located below barrier member 90 is another plastic (e.g. TEFLON™) washer 92, and below that a second stainless steel plate 94, also shown in FIG. 10. Plate 94 in the example shown was 29 mm by 29 mm, by 4 mm thick, and had an interior opening 96 which was 18 mm by 18 mm. Four tubular drains 98 (e.g. 2.3 mm diameter) extend from each side of opening 96. Glued to the bottom of plate 4 and covering opening 96 is a glass window 100. The space between shim 90 and window 100 defines a lower chamber 102, which in the example shown was (including the 1 mm to 2 mm thickness of washer 22) approximately 5 mm to 6 mm thick.

A sheath fluid is supplied from source 110. The sheath fluid is chosen to have the same or a similar index of refraction as the aqueous buffer used to prepare the polymer mixture which fills the capillary tubes 26. The sheath fluid enters the chamber 34 via openings or inlets 56 in the plate 40, and is pumped from source 110 in a non-pulsating flow, e.g. by a simple gravity feed (under a head, for example, of about 5 cm) or by a very low pulsation pumping means such as a high quality syringe pump (not shown). The sheath fluid flows through the holes 80 in the barrier member 90 and into the lower chamber 102, from which it drains via the four tubular openings 98 and drain tubes 112. As described in our above-mentioned patent, droplet formation should be avoided, e.g. by draining the sheath fluid (including the flow from the capillary tubes as will be described) into a beaker 114 in which drain tubes 112 are submerged. Beaker 114 in turn drains into beaker 116, which drains to waste.

Figure 11:
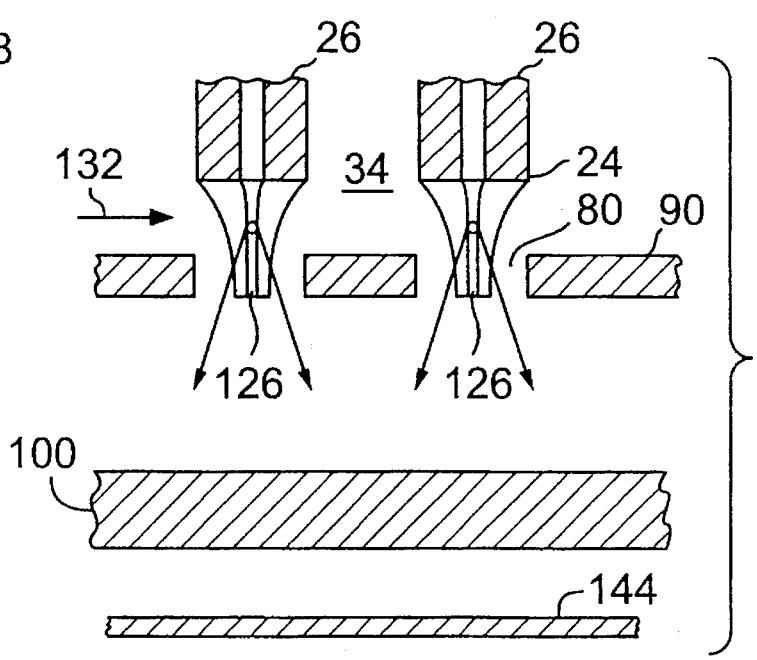
FIG. 11 is an enlarged cross-sectional view of two capillaries and other components of the analyzer system of FIG. 1.

A high voltage source 120 is provided, having one pole 122 connected through conductive plate 32 to the fluid in each of the wells 30. The other pole 124 of the source 120 is connected to the tab 54 of the plate 40, which tab is grounded for safety reasons. The source 120 provides a driving voltage of e.g. 30 kV which, via the fluid in chamber 34, appears across the length of the capillaries 26. As is well known, the electric field created by the voltage source 120 causes fragments of sample DNA from the wells 30 to migrate through the matrix or gel in the capillaries 26. At the ends 24 of the capillary tubes 26, the sheath fluid entrains sample fluid from the capillaries, in the form of individual filaments 126 of fluid, as best shown in FIG. 11. The filaments are aligned with holes 80 in barrier member 90 and pass through those holes 80 together with the sheath fluid. In the lower chamber 102, the filaments 126 mingle with the sheath fluid, and the mixed fluids are drained via openings 98.

A laser 130 or other source of collimated electromagnetic radiation provides a collimated beam 132 of light that is aligned to pass from a focusing lens 134 into the chamber 34, as close as possible above the barrier member 90. Preferably the laser beam 132 is elliptically shaped, to illuminate all of the sample streams simultaneously. Alternatively, the beam 132 may be split into a set of parallel beams with appropriate optics, with one parallel beam per row of capillaries. Fluorescence is excited in the chamber 34, above the barrier member 90. The fluorescence passes through the holes 80 in barrier member 90, through the glass window 100 at the bottom of lower chamber 102, and through a two element air-spaced condenser lens 136, typically operated at unit magnification. The condenser 136 images the fluorescence onto a photodetector 138. A spectral filter shown diagrammatically in dotted lines at 139 may be used to isolate fluorescence from specific dyes. The filter 139 can be a tunable filter, or a set of filters on a rotating wheel, or can be a grating or a prism. The filter 139 is preferably placed in the space between the lenses of condenser 136 since that is where the light is relatively well collimated and the light rays strike the filter roughly at right angles. If the filters were placed in the diverging portion of the beam either before or after condenser 136, then the spectrum of the transmitted light would vary across the aperture of the filter, since the transmitted spectrum depends on the incident angle,.

Preferably the photodetector 138 is a large area CCD chip of a CCD camera 140. The area of chip 138 is as large as or larger than the area of the capillary array, thus providing high collection efficiency. (If desired the window 100 can be a lens or can even be a part of the CCD camera 140.) The chip 138 is connected to a computer 142 so that the chip output can be analyzed.

The arrangement shown has several advantages. One advantage is that the photodetector looks straight, end-on, at the capillaries, so optical correction elements are not needed to obtain a high quality picture of the fluorescence. In addition, the path length through the fluid is the same for the fluorescence from each filament or sample stream 126, so no distortion is introduced due to differing path lengths. The barrier member 90 ensures that the individual sample filaments 126 will remain intact above the barrier member 90 (i.e. in the region where they are being illuminated), so that the fluorescing spots can be looked at end-on, even though below the barrier member 90 the filaments 126 lose their individual character. The flow in lower chamber 102 should preferably be non-turbulent, but with the low flow rates used, turbulent flow would be highly unlikely to occur. (For DNA sequencing, where there is no bulk solvent flow through capillaries, but instead the analyte molecules are drawn from the tip of the capillaries and entrained in the sheath fluid stream, the flow is essentially only the sheath fluid flow, which may typically be about 10 microliters/minute per capillary, or e.g. 0.25 milliliters/minute for a 25 capillary design and 1 milliliters/minute for a 96 capillary design. In non-DNA analysis, the flow would be augmented by a sample flow rate of typically 0.1 to 1 microliters/minute from each capillary.)

Secondly, the sandwich construction shown holds the capillaries on fixed centers in a leak-proof manner, so there is no need to worry about proper alignment of the capillaries.

Thirdly, the barrier member 90 blocks a substantial amount of scattered laser light from reaching the photodetector, e.g. the CCD chip 138. The reduced fluorescence background allows a higher signal to noise ratio and improved accuracy of results.

While close spacing of the capillaries is normally preferred, if desired they can be spaced further apart (e.g. by more than one capillary outer diameter), and a diffraction grating (shown at 144 in FIG. 11) can be inserted between window 100 and the camera 140, to disperse the emission spectrum from each fluorescing spot, to help determine DNA sequences or for other analysis.

In assembly of the cuvette 22 shown in FIG. 2, the upper part of the cuvette is first assembled, consisting of shims 62, 64, 66 and their associated washers. This assembly is placed on a plate such as bottom plate 94, which itself is placed on a flat, smooth, solid surface. The capillary tubes 26 are then threaded through the holes 80 in shims 62, 64, 66, in the process creating the holes in rubber washer or disc 84, until the capillary tubes reach the bottom supporting surface. This ensures that the ends 24 of the capillary tubes 26 lie in a plane. When the entire chamber is assembled, the plane in which the capillary ends 24 lie is, in the example shown, about 1 mm above the barrier member 90.

Figure 12:
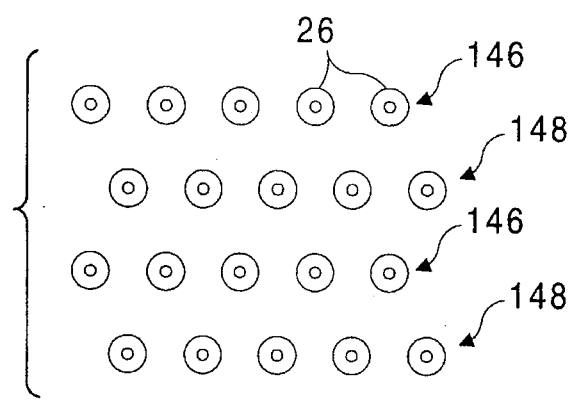
FIG. 12 shows a modified capillary array for the analyzer of FIG. 1.

While a rectangular array of capillary tubes 26 has been shown, if desired other forms of array can be used, e.g. a configuration as shown in FIG. 12, where alternate rows 146 are offset so that they are located in the spaces between adjacent rows 148. More dense packing is advantageous for efficient illumination and detection. If the spacing is too large, there may be poor optical excitation and collection efficiency, since it is difficult to focus a laser beam over the large area defined by widely spaced capillaries, and it can be difficult to collect fluorescence from widely spaced capillaries. However the use of a large area CCD chip 132 will solve this latter problem, and the use of the opaque barrier member 90 blocks scattered light which can be generated by a non-ideally focused laser beam.

In the embodiment described, the driving force created by the electric field applied across the capillary tubes 26 is limited to the capillaries and the sample stream filaments are drawn from the capillaries by the sheath fluid. If desired other driving means may be used for the sample, as described in our above-mentioned patent. For example the sample can be forced through the capillary tubes 26 by an appropriate pump, as in flow cytometry. In addition the number of capillary tubes in the array used can vary. For example 96 capillaries in a 12 by 8 array may be used, to interface with a 96 well microtiter plate. By way of further example, 864 capillaries may be used in a 36 by 24 array to interface with an 864 well microtiter plate. Other arrays can be designed as needed.

While preferred embodiments of the invention have been described, it will be understood that modifications may be made within the spirit of the invention and all such modifications are intended to be encompassed by the appended claims.

I claim:

1. An analyzer for analyzing an organic sample, said analyzer comprising:

(a) a plurality of capillary tubes arranged side by side, each capillary tube having first and second ends, the second ends of the capillary tubes terminating adjacent each other and the first ends being connectable to a source of organic sample, (b) a flow chamber having an interior cavity, the second ends of the capillary tubes terminating inside the interior cavity, (c) means to force said organic sample through the capillary tubes from the first ends of the capillary tubes to the second ends of the capillary tubes, (d) means to provide sheath fluid into the interior cavity of said flow chamber to provide a flow of sheath fluid past the secondly ends of the capillary tubes and for entraining organic sample from said capillary tubes in individual sample streams from the second ends of the capillary tubes, (e) a barrier member spaced from the second ends of said capillary tubes, said barrier member including a plurality of openings therein, said openings being aligned with said second ends of said capillary tubes for the individual sample streams therefrom to pass through said openings, said barrier member having a first side facing said second ends of said capillary tubes, and a second side opposite said first side, (f) radiation means providing electromagnetic radiation having a wavelength that may excite said sample to emit radiation, said radiation means being positioned to illuminate said sample streams between said second ends of said capillary tubes and said first side of said barrier member, (g) and radiation detection means on said second side of said barrier means for detecting radiation which is emitted from said sample streams and which passes through said openings to said second side of said barrier member.

2. An analyzer according to claim 1 wherein said radiation means provides a beam of collimated electromagnetic radiation which extends through said sample streams immediately adjacent said first side of said barrier member.

3. An analyzer according to claim 2 and including a window located on said second side of said barrier member, said window defining with said barrier member a collection chamber for collecting sheath fluid and said sample streams from said capillary tubes, and a drain in said collection chamber for drawing collected fluids from said collection chamber.

4. An analyzer according to claim 3 wherein said barrier member has the form of a thin flat opaque plate.

5. An analyzer according to claim 4 wherein said radiation detection means includes a CCD camera chip.

6. An analyzer according to claim 4 wherein said second ends of said capillary tubes are all spaced a uniform distance from said first side of said barrier member.

7. An analyzer according to claim 6 wherein said distance does not exceed about 1 mm.

8. The analyzer according claim 4 wherein said window is spaced within approximately 5 mm to 6 mm of said second side of said barrier member.

9. An analyzer according to any preceding claim and including an electrophoretic voltage source connected across said capillary tubes to force said organic sample through said capillary tube from said first ends to said second ends.

10. An analyzer according to any of claims 1 to 4 wherein said second ends of said capillary tubes are arranged in a plurality of rows, each row containing a plurality of capillary tubes.

11. An analyzer according to any of claims 1 to 4 and including sandwich means for retaining said second ends of said capillary tubes in said interior cavity, said sandwich means comprising a pair of rigid plates and a resilient spacer between them, said rigid plates and said resilient spacer containing aligned holes therethrough for said capillary tubes to pass therethrough, and means for squeezing said rigid plates towards each other against said resilient spacer for said resilient spacer to form a liquid-tight seal around said capillary tubes.

12. An analyzer according to any of claims 1 to 4 and including spectrum dispersing means for dispersing the spectrum of radiation emitted from said sample streams after said radiation has passed through said openings in said barrier member.

13. An analyzer according to any of claims 1 to 4 and including a spectral filter associated with said radiation detection means for isolating a selected radiation band from radiation emitted from said sample streams.

* * * * *